United States Patent
Osaki et al.

(10) Patent No.: US 10,106,520 B2
(45) Date of Patent: Oct. 23, 2018

(54) APPARATUS AND METHOD FOR PRODUCING CYCLIC CARBONATE

(71) Applicant: MARUZEN PETROCHEMICAL CO., LTD., Chuo-ku (JP)

(72) Inventors: Kouzo Osaki, Funabashi (JP); Takashi Naniki, Ichihara (JP); Yasunori Hayashi, Ichihara (JP); Takeshi Haruna, Chiba (JP)

(73) Assignee: MARUZEN PETROCHEMICAL CO., LTD., Chuo-ku (JP)

( * ) Notice: Subject to any disclaimer, the term of this patent is extended or adjusted under 35 U.S.C. 154(b) by 0 days.

(21) Appl. No.: 15/314,804

(22) PCT Filed: May 29, 2015

(86) PCT No.: PCT/JP2015/065492
§ 371 (c)(1),
(2) Date: Nov. 29, 2016

(87) PCT Pub. No.: WO2015/182732
PCT Pub. Date: Dec. 3, 2015

(65) Prior Publication Data
US 2017/0197931 A1 Jul. 13, 2017

(30) Foreign Application Priority Data
May 30, 2014 (JP) .................................. 2014-112219

(51) Int. Cl.
*B01J 8/00* (2006.01)
*B01J 8/02* (2006.01)
(Continued)

(52) U.S. Cl.
CPC .......... *C07D 317/38* (2013.01); *B01J 8/0457* (2013.01); *B01J 2208/027* (2013.01); *C07B 61/00* (2013.01); *Y02P 20/544* (2015.11)

(58) Field of Classification Search
CPC ......... B01J 8/00; B01J 8/02; B01J 8/04; B01J 8/0446; B01J 8/0449; B01J 8/0457;
(Continued)

(56) References Cited

U.S. PATENT DOCUMENTS 4,729,664 A 3/1988 Kamiwano et al.
8,735,608 B2 5/2014 Zhang et al.
(Continued)

FOREIGN PATENT DOCUMENTS

JP 62-117623 A 5/1987
JP 63-17072 B2 4/1988
(Continued)

OTHER PUBLICATIONS

International Search Report dated Aug. 4, 2015 in PCT/JP2015/065492 filed May 29, 2015.
"Report on the research and development achievement on the environmental load reduction technology utilizing supercritical fluid," 14-3, (21 pages, with Partial English Translation).

*Primary Examiner* — Natasha E Young
(74) *Attorney, Agent, or Firm* — Oblon, McClelland, Maier & Neustadt, L.L.P.

(57) ABSTRACT

An apparatus and method for continuously producing a cyclic carbonate which are easily scaled up without requiring a large-sized reactor or excessive ancillary facilities even in the case of producing a cyclic carbonate by using an immobilized catalyst as a catalyst on an industrial scale, are able to produce a cyclic carbonate without impairing the expected catalytic efficiency and catalyst lifetime, are economical, and exhibit excellent industrial productivity. The apparatus includes an adiabatic reactor to be filled with a heterogeneous catalyst for reacting an epoxide with carbon dioxide, a circulation path for returning at least a portion of a fluid mixture in a liquid form flowed out through a reactor outlet into the reactor, a carbon dioxide supply means for continuously supplying carbon dioxide in a liquid form or a
(Continued)

supercritical state into the circulation path, and an epoxide supply means.

20 Claims, 2 Drawing Sheets

(51) Int. Cl.
*B01J 8/04* (2006.01)
*B01J 19/00* (2006.01)
*B01J 19/24* (2006.01)
*C07C 317/38* (2006.01)
*C07D 317/38* (2006.01)
*C07B 61/00* (2006.01)

(58) Field of Classification Search
CPC ........ B01J 19/00; B01J 19/24; B01J 2208/02; B01J 2208/023; B01J 2208/027; B01J 2219/24; C07D 317/00; C07D 317/08; C07D 317/10; C07D 317/32–317/38; C07D 317/26

See application file for complete search history.

(56) References Cited

U.S. PATENT DOCUMENTS

| | | |
|---|---|---|
| 2006/0281929 A1 | 12/2006 | Okamoto et al. |
| 2008/0214386 A1 | 9/2008 | Takahashi et al. |
| 2013/0225840 A1* | 8/2013 | Zhang .................. C07D 317/38 549/230 |
| 2014/0221672 A1 | 8/2014 | Zhang et al. |
| 2016/0145234 A1 | 5/2016 | Takahashi et al. |
| 2016/0168112 A1 | 6/2016 | Naniki et al. |

FOREIGN PATENT DOCUMENTS

| | | |
|---|---|---|
| JP | 11-335372 A | 12/1999 |
| JP | 2008/229505 A | 10/2008 |
| WO | 2004/108696 A1 | 12/2004 |
| WO | 2005/084801 A1 | 9/2005 |
| WO | 2013/130147 A1 | 9/2013 |
| WO | 2015/008853 A1 | 1/2015 |
| WO | 2015/008854 A1 | 1/2015 |

\* cited by examiner

APPARATUS AND METHOD FOR PRODUCING CYCLIC CARBONATE

This application is a U.S. national stage application of International Patent Application No. PCT/JP2015/065492, now WO 2015/182732, filed on May 29, 2015, which claims priority to European Patent Application No. JP 2014-112219, filed on May 30, 2014, which is hereby expressly incorporated by reference in its entirety.

TECHNICAL FIELD

The present invention relates to an apparatus and a method for producing a cyclic carbonate. More particularly, it relates to an apparatus and a method for producing a cyclic carbonate by reacting an epoxide with carbon dioxide in the presence of a heterogeneous catalyst.

BACKGROUND ART

Cyclic carbonates are an important compound used in a wide range of applications as they are used as an organic solvent, a synthetic fiber processing agent, a pharmaceutical raw material, and a cosmetic additive, also recently used as an electrolyte solvent for lithium batteries, and further utilized in the synthesis of alkylene glycols or dialkyl carbonates.

This cyclic carbonate has been conventionally synthesized by reacting an epoxide with carbon dioxide in the presence of a homogeneous catalyst under a proper pressurized condition. As such a homogeneous catalyst, an onium salt such as a halide or a quaternary ammonium salt of an alkali metal, for example, has long been known (Patent Literature 1), and such a homogeneous catalyst is also industrially used.

However, the separation operation of the reaction mixture from the catalyst by, for example, distillation is usually required in the case of using such a homogeneous catalyst, and thus not only the producing process is complicated but there is also a problem such as the decomposition of the catalyst during the separation process or the generation of by-products.

Accordingly, a heterogeneous catalyst in which a quaternary phosphonium group having a halide ion as a counter ion is immobilized on a support such as silica gel has been proposed for the purpose of simplifying the catalyst separation process, and a method for continuously producing propylene carbonate by mixing propylene oxide with supercritical carbon dioxide and supplying the mixture to the reaction tube filled with the immobilized catalyst is disclosed as a method for producing propylene carbonate using the immobilized catalyst (Patent Literature 2).

However, the immobilized catalyst exhibits lower activity as compared to a homogeneous catalyst, and thus it is required to be used in a great amount and it is a problem to increase the reactor in size particularly in the case of producing a cyclic carbonate on an industrial scale.

In addition, the passing amount of the reaction solution with respect to the catalyst amount is smaller, and thus there is a problem that (1) the uneven flow of the reaction solution occurs in the reactor and (2) the contact of the catalyst with the reaction solution, namely, wetting of the catalyst becomes insufficient and thus the catalyst is not able to sufficiently function. Furthermore, for example, the uneven flow in the system causes a factor of hot spots (local overheating of the catalyst) and the deterioration of catalyst is significantly accelerated.

On the other hand, the uneven flow is generated in the system or wetting of the catalyst is insufficient, and as a result, a decrease in catalytic efficiency and catalyst lifetime is likewise caused in the same manner as the above, in a case that carbon dioxide is gasified in the reactor.

In addition, the reaction solution does not necessarily form a homogeneous phase when carbon dioxide is insufficiently mixed even under the condition in which carbon dioxide is not gasified. For example, propylene oxide and supercritical carbon dioxide are used by being mixed in Patent Literature 2, and the phase separation between propylene carbonate of the product and supercritical carbon dioxide is caused as described in Non Patent Literature 1. Hence, carbon dioxide is required to be completely mixed with the reaction solution in order to sufficiently dissolve carbon dioxide in the reaction solution and to suppress the phase separation in the reactor, and thus a large-scale ancillary facility such as a stirring tank is required.

Furthermore, when the temperature increases, the catalyst component is desorbed from the immobilized catalyst and the activity of the immobilized catalyst significantly decreases, whereas the reaction of an epoxides with carbon dioxide is an exothermic reaction to release a relatively great quantity of reaction heat (for example, the reaction heat released by the reaction of ethylene oxide with carbon dioxide is about 100 kJ/mol), and thus the removal of reaction heat at the time of the synthesis of a cyclic carbonate is a problem in the case of using an immobilized catalyst.

As the method for removing the react ion heat, it is a general method to use a heat exchanger-type reactor such as a jacketed reactor or a multi-tubular reactor.

However, the heat removal by a jacketed reactor to circulate the heat medium to the jacket has a basic problem that the heat removal area decreases as compared to the amount of catalyst when the reactor is increased in size and only the heat from the immobilized catalyst in the vicinity of the heat removal surface can be removed.

On the other hand, in the case of a multi-tubular reactor having a plurality of reaction tubes provided in the reactor shell, the reaction heat generated is removed by circulating the heat medium in the reaction tube shell while the reaction is conducted by filling the catalyst in the reaction tube, and thus it is possible to increase the heat removal area. However, in the case of using a catalyst immobilized on a support such as silica gel, a significantly little liquid flows as compared to this amount of catalyst flows, thus the reaction tube is required to be significantly thin and long in order to obtain a sufficient heat removal efficiency, and the apparatus is complicated and increased in size. In addition, the maintenance is also troublesome. Furthermore, there is also a problem that it is difficult to uniformly fill a plurality of reaction tubes with a catalyst.

CITATION LIST

Patent Literature

Patent Literature 1: JP 63-17072 B
Patent Literature 2: WO 2005/084801 A

Non Patent Literature

Non Patent Literature 1: Report on the research and development achievement on the environmental load reduction technology utilizing supercritical fluid, March 2002, National Institute of Advanced Industrial Science and Technology

SUMMARY OF INVENTION

Technical Problem

As described above, an excessively large-scale apparatus including a large-sized reactor, a cooling facility, and a mixing facility as compared to the production quantity is required when a cyclic carbonate is produced on an industrial scale by using an immobilized catalyst. In addition, there is also a problem that scaling up is not easy in the case of a process requiring such a large-sized reactor or ancillary facilities.

Accordingly, an object of the present invention is to provide an apparatus and method for continuously producing a cyclic carbonate which are easily scaled up without requiring a large-sized reactor or excessive ancillary facilities even in the case of producing a cyclic carbonate by using an immobilized catalyst as a catalyst on an industrial scale, are able to produce a cyclic carbonate without impairing the expected catalytic efficiency and catalyst lifetime, are economical, and exhibit excellent industrial productivity.

Solution to Problem

In order to achieve the above object, [1] the present invention provides an apparatus for producing a cyclic carbonate including:

an adiabatic reactor to be filled with a heterogeneous catalyst for reacting an epoxide with carbon dioxide;

a circulation path for returning at least a portion of a fluid mixture in a liquid form flowed out through a reactor outlet into the reactor;

a carbon dioxide supply means for continuously supplying carbon dioxide in a liquid form or a supercritical state into the circulation path; and an epoxide supply means for continuously supplying an epoxide in a liquid or solution form into the circulation path, in which the circulation path includes a heat exchange means for removing heat from a circulating fluid (fluid mixture in a liquid form flowed into a circulating path) by indirect heat exchange, a mixing means for mixing carbon dioxide supplied by the carbon dioxide supply means with the circulating fluid in a path, a gas-liquid separation means for conducting a gas-liquid separation treatment by reducing the pressure of a circulating fluid containing carbon dioxide obtained by the mixing means, a pressurization means for pressurizing a circulating fluid after the gas-liquid separation treatment to a predetermined pressure, and a mixing means for mixing the epoxide supplied by the epoxide supply means with the circulating fluid in a path.

In addition, in order to achieve the above object, [2] the present invention provides the apparatus for producing a cyclic carbonate according to [1], wherein the reactor is configured as a fixed bed multi-stage reactor by two or more adiabatic reactors connected in series, and the circulation path is provided so as to return at least a portion of a fluid mixture in a liquid form flowed out through an outlet of a last stage reactor to a first stage reactor.

In the present invention, the amount of catalyst with respect to the production quantity of a cyclic carbonate is approximately constant regardless of the number of reactors, and thus it is easy to enhance the production capacity by increasing the number of reactors in the producing apparatus according to [2].

Furthermore, in order to achieve the above object, [3] the present invention provides a method for producing a cyclic carbonate by continuously supplying a raw material fluid mixture containing an epoxide and carbon dioxide to an adiabatic reactor filled with a heterogeneous catalyst and leading at least a portion of a fluid mixture in a liquid form flowed out through a reactor outlet to a circulation path and returning to the reactor, the method including:

a heat exchange step of removing heat from a circulating fluid (fluid mixture in a liquid form flowed into a circulating path) by indirect heat exchange;

a carbon dioxide supply step of continuously supplying carbon dioxide in a liquid form or a supercritical state into the circulation path;

a mixing step of mixing carbon dioxide supplied in the carbon dioxide supply step with the circulating fluid in a path;

a gas-liquid separation step of reducing the pressure of a circulating fluid containing carbon dioxide obtained in the mixing step and conducting the gas-liquid separation treatment of excess carbon dioxide gasified;

a pressurization step of pressurizing a circulating fluid after gas-liquid separation to a predetermined pressure;

an epoxide supply step of continuously supplying an epoxide in a liquid or solution form to the circulation path; and a mixing step of mixing the epoxide supplied in the epoxide supply step with the circulating fluid in a path.

Furthermore, in order to achieve the above object, [4] the present invention provides the method for producing a cyclic carbonate according to [3], wherein the reactor is configured as a fixed bed multi-stage reactor by two or more adiabatic reactors connected in series, and the circulation path is to return at least a portion of a fluid mixture in a liquid form flowed out through an outlet of a last stage reactor to a first stage reactor.

In the present invention, the amount of catalyst with respect to the production quantity of a cyclic carbonate is approximately constant regardless of the number of reactors, and thus it is easy to enhance the production capacity by increasing the number of reactors in the producing method according to [4].

Advantageous Effects of Invention

According to the present invention, it is possible to provide an apparatus and method for continuously producing a cyclic carbonate which are able to be easily scaled up by increasing the number of reactors without requiring a large-sized reactor or excessive ancillary facilities, are able to produce a cyclic carbonate without impairing the expected catalytic efficiency and catalyst lifetime by suppressing the uneven flow or phase separation of the reaction solution and efficiently removing the reaction heat, are economical, and exhibit excellent industrial productivity.

DESCRIPTION OF EMBODIMENTS

Figure 1:
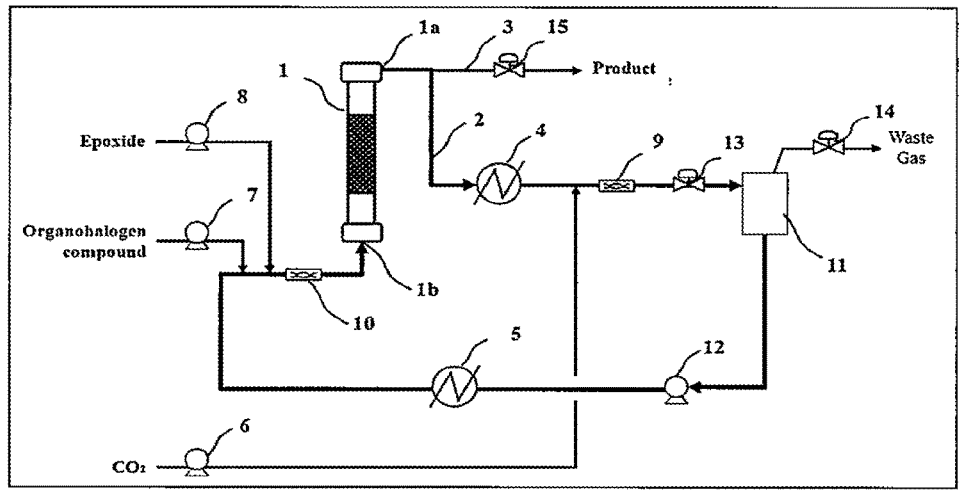
FIG. 1 is a diagram schematically illustrating an example of a first embodiment of the apparatus for producing a cyclic carbonate of the present invention.

Hereinafter, the present invention will be described with reference to the accompanying drawings if necessary. Incidentally, the same elements in the description of the drawings are denoted by the same reference numerals, and duplicate description thereof is omitted.

First, the raw material epoxide and the heterogeneous catalyst to be used in the present invention and the cyclic carbonate obtained in the present invention will be described.

(Epoxide)

The epoxide to be used in the present invention is not particularly limited as long as it is a compound containing at least one epoxy ring (3-membered ring composed of two carbon atoms and one oxygen atom) in the structural formula, and examples thereof may include ethylene oxide, propylene oxide, butylene oxide, isobutylene oxide, vinylethylene oxide, trifluoromethylethylene oxide, cyclohexene oxide, styrene oxide, butadiene monoxide, butadiene dioxide, 2-methyl-3-phenyl-butene oxide, pinene oxide, and tetracyanoethylene oxide.

Among such epoxides, those represented by the following formula (1) are preferable, and ethylene oxide and propylene oxide are more preferable.

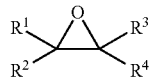

[In the formula (1), $R^1$ and $R^2$ each independently represent a hydrogen atom, an alkyl group having from 1 to 6 carbon atoms, a haloalkyl group having from 1 to 6 carbon atoms, an alkenyl group having from 2 to 6 carbon atoms, a haloalkenyl group having from 2 to 6 carbon atoms, an aryl group having from 6 to 12 carbon atoms, or a cyano group, $R^3$ and $R^4$ each independently represent a hydrogen atom, a cyano group, or an aryl group having from 6 to 12 carbon atoms. However, either one of $R^3$ or $R^4$ may form a cycloalkyl group together with either one of $R^1$ or $R^2$.]

The number of carbon atoms in the alkyl group and haloalkyl group represented by $R^1$ and $R^2$ is preferably from 1 to 4. Examples of the alkyl group may include a methyl group, an ethyl group, a propyl group, and a butyl group, preferably a methyl group and an ethyl group, and more preferably a methyl group.

In addition, the number of carbon atoms in the alkenyl group and haloalkenyl group represented by $R^1$ and $R^2$ is preferably from 2 to 4, and specific examples thereof may include a vinyl group.

In addition, examples of the halogen atom in the haloalkyl group and haloalkenyl group may include chlorine, bromine, and iodine.

In addition, as the aryl group represented by $R^1$, $R^2$, $R^3$, and $R^4$, a phenyl group is preferable.

In addition, among $R^1$ and $R^2$, a hydrogen atom, an alkyl group having from 1 to 6 carbon atoms, and a haloalkyl group having from 1 to 6 carbon atoms are preferable.

In addition, as $R^3$ and $R^4$, a hydrogen atom is preferable.

(Heterogeneous Catalyst)

As the heterogeneous catalyst to be used in the present invention, an immobilized catalyst which exhibits activity in the synthesis of a cyclic carbonate from an epoxide and carbon dioxide is preferable, and a solid catalyst in which an ionic organic compound is immobilized on a support is more preferable.

Examples of such an ionic organic compound may include a quaternary organic onium salt selected from a quaternary organic ammonium salt having a halide anion as a counter ion and a quaternary organic phosphonium salt having a halide anion as a counter ion. Examples of the halide anion may include a fluorine anion, a chlorine anion, a bromine anion, and an iodine anion.

Suitable specific examples of the quaternary organic onium salt may include a tetraalkylammonium salt such as tetraalkylammonium chloride or tetraalkylammonium bromide; and a tetraalkylphosphonium salt such as tetraalkylphosphonium chloride or tetraalkylphosphonium bromide, and a tetraalkylphosphonium salt is preferable among them.

In addition, the number of carbon atoms in the alkyl group in the tetraalkylammonium salt and the tetraalkylphosphonium salt is preferably from 1 to 8, more preferably from 1 to 6, and even more preferably from 2 to 4. Examples thereof may include a methyl group, an ethyl group, a propyl group, an isopropyl group, a butyl group, an isobutyl group, a pentyl group, a hexyl group, a heptyl group, an octyl group, and a cyclohexyl group.

In addition, examples of the support may include an inorganic oxide support and an organic polymer support. In addition, the shape thereof is preferably a particle shape and a porous one is preferable. Suitable specific examples of the inorganic oxide support may include silica (gelled silica), mesoporous silica, ceramics, zeolite, and porous glass, and silica and mesoporous silica are preferable among them. In addition, examples of the organic polymer support may include polystyrene, a polystyrene copolymer, a poly(meth)acrylate, a poly(meth)acrylamide, a polyimide, polybenzimidazole, polybenzoxazole, polybenzothiazole, polyethylene glycol, polypropylene glycol, or a copolymer containing these polymers as a main component, and a polymer blend.

(Cyclic Carbonate)

In addition, the cyclic carbonate obtained in the present invention is one that has a structure in which the epoxy ring of the epoxide is converted to a carbonate ring (5-membered ring having O—CO—O bonding), and examples thereof may include ethylene carbonate, propylene carbonate, butylene carbonate, isobutylene carbonate, trifluoromethyl ethylene carbonate, vinyl ethylene carbonate, cyclohexene carbonate, styrene carbonate, butadiene monocarbonate, butadiene dicarbonate, chloromethyl carbonate, pinene carbonate, and tetracyanoethylene carbonate. Suitable cyclic carbonate is those represented by the following formula (2).

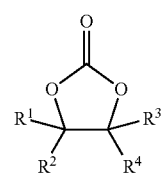

[In the formula (2), $R^1$ to $R^4$ have the same meaning as described above.]

[(1) Apparatus for Producing Cyclic Carbonate]

First Embodiment

The apparatus for producing a cyclic carbonate relating to the first embodiment of the present invention (first producing apparatus) will be described.

FIG. 1 is a diagram schematically illustrating an example of the apparatus for producing a cyclic carbonate relating to the first embodiment of the present invention.

As illustrated in FIG. 1, the producing apparatus of the present embodiment includes an adiabatic reactor 1 to be filled with a heterogeneous catalyst for reacting an epoxide with carbon dioxide, a circulation path 2 for returning at least a portion of the fluid mixture in a liquid form flowed out through a reactor outlet 1a into the reactor 1, and a discharge path 3 for discharging the remainder of the fluid mixture in a liquid form and sending it to the next step if necessary. The fluid mixture in a liquid form flowed out through the reactor outlet 1a mainly contains the cyclic carbonate produced in the reactor 1 and unreacted carbon dioxide, and it also may contains the unreacted epoxide depending on the reaction conditions.

The reactor 1 may be an adiabatic reactor that is configured so as to be able to be filled with the heterogeneous catalyst for reacting an epoxide with carbon dioxide, and a tubular reactor is preferable. In addition, the material constituting the reactor 1 is not particularly limited, and it is preferably SUS from the viewpoint of excellent corrosion resistance. In addition, it is possible to greatly cut down the facility cost by using an inexpensive adiabatic reactor as the reactor 1.

In addition, for example, glass beads may be filled before or after the catalyst when the heterogeneous catalyst is filled in the reactor 1.

In addition, the reactor 1 is provided with a reactor inlet 1b. The reactor inlet 1b is configured such that the circulating fluid flows from the circulation path 2 into the reactor 1, the circulating fluid formed as carbon dioxide and an epoxide are supplied to and mixed in the circulation path 2 is supplied into the reactor 1 through the reactor inlet 1b as a raw material fluid mixture.

In addition, the producing apparatus of the present embodiment includes a carbon dioxide supply means 6 for continuously supplying carbon dioxide in a liquid form or a supercritical state into the circulation path 2 and an epoxide supply means 8 for continuously supplying an epoxide in a liquid or solution form into the circulation path 2.

By the carbon dioxide supply means 6, carbon dioxide of a reaction raw material is continuously supplied to the circulating fluid in a liquid form or a supercritical state, and by the epoxide supply means 8, the epoxide of a reaction raw material is continuously supplied to the circulating fluid in a state of being a liquid or solution. In addition, the supply amounts of carbon dioxide and the epoxide are controlled by these configurations.

Examples of the carbon dioxide supply means 6 and epoxide supply means 8 may include a pump. By employing a pump as these means, it is possible to easily control the supply amount of carbon dioxide or the epoxide. In addition, it is also possible to greatly cut down the facility cost.

Incidentally, in the epoxide supply means 8, it is preferable to use the cyclic carbonate to be synthesized from the epoxide as the solvent in the case of supplying the epoxide in a solution form dissolved in a solvent. Specifically, the solvent is preferably ethylene carbonate in the case of supplying ethylene oxide in a solution form dissolved in a solvent.

In addition, the producing apparatus of the present embodiment may include an additive supply means 7 for supplying an additive other than the reaction raw materials into the circulation path 2. By the additive supply means 7, the additive is supplied into the circulation path 2 while the supply amount is controlled.

The additive may be supplied continuously or discontinuously. In addition, the additive may be supplied in neat or in a solution form dissolved in a solvent. The solvent is preferably a cyclic carbonate in the case of supplying the additive in a solution form dissolved in a solvent.

Examples of the additive supply means 7 may include a pump.

In addition, examples of the additive may include a halogenated alcohol such as bromoethanol or bromopropanol. A halogenated alcohol suppresses desorption of the catalyst component and acts as an inhibitor of catalyst deterioration.

In addition, the producing apparatus of the present embodiment includes the circulation path 2. In the circulation path 2, a heat exchange means 4, a first mixing means 9, a gas-liquid separation means 11, a pressurization means 12, and a second mixing means 10 are provided from the reactor outlet 1a toward the direction of the reactor inlet 1b in the order of the heat exchange means 4, the first mixing means 9, the gas-liquid separation means 11, the pressurization means 12, and the second mixing means 10.

By the circulation path 2, a portion of the fluid mixture in a liquid form flowed out through the reactor outlet 1a is circulated to the reactor 1, and as a result, the liquid flow in the reactor 1 increases, the temperature rise in the reactor 1 is likely to be suppressed in an appropriate range, and the uneven flow of the reaction solution or the poor wetting of the catalyst in the reactor 1 can be eliminated, and thus it is possible to suppress a decrease in catalytic efficiency or catalyst lifetime. Furthermore, it is possible to extend the retention time and thus it is possible to decrease the amount of catalyst and the size of the reactor 1 to be compact.

The circulation path 2 is configured as an arbitrary proper pipe. The material constituting the pipe is not particularly limited, and it is preferably SUS from the viewpoint of excellent corrosion resistance.

In addition, the circulation path 2 includes the heat exchange means 4 for removing heat from the circulating fluid by indirect heat exchange.

By providing the circulation path 2 with the heat exchange means 4, the reaction heat can be easily removed, and thus it is possible to easily control the temperature in the reactor 1 in a desired range (substantially the reaction temperature). It is not possible to sufficiently remove the reaction heat in the case of not providing the heat exchange means 4, and thus the temperature in the reactor 1 increases and the catalyst lifetime is extremely shortened in some cases.

As the heat exchange means 4, an arbitrary heat exchanger can be used as long as it can remove the reaction heat by lowering the temperature of the circulating fluid passing through the means. Specific examples thereof may include a multi-tubular cylindrical heat exchanger, a double tube heat exchanger, a plate heat exchanger, an air cooler, an irrigation cooler, a coil heat exchanger, and a scroll heat exchanger, and the circulating flow rate is relatively a small flow rate and the operation is conducted at a high pressure, and thus a double tube heat exchanger, an air cooler, and an irrigation cooler are particularly proper and preferable. In addition, the overall heat transfer coefficient of these heat exchangers is preferably about 200 kcal/(m² hrK) or more.

In addition, it is preferable that only the circulation path 2 is configured in between the reactor outlet 1*a* and the heat exchange means 4. By such a configuration, the circulating fluid flowed out through the reactor outlet 1*a* is to be quickly subjected to the heat removal.

In addition, in the circulation path 2, the carbon dioxide inflow portion into which carbon dioxide supplied by the carbon dioxide supply means 6 flows is not particularly limited, and it may be at any place in the circulation path, and carbon dioxide exhibits a low thermal conductivity and the solubility thereof increases as the temperature decreases, and thus it is preferable to supply to the circulating fluid after heat removal and quickly mix it with carbon dioxide. Accordingly, the carbon dioxide inflow portion is preferably provided in between the heat exchange means 4 and the mixing means 9.

In addition, the circulation path 2 includes the mixing means 9 (first mixing means) for mixing carbon dioxide supplied by the carbon dioxide supply means 6 with the circulating fluid which flows into the circulation path 2 and is subjected to the heat removal by the heat exchange means 4 in the path.

By the mixing means 9, the supplied carbon dioxide is homogeneously mixed with other components.

As the mixing means 9, it is preferable to use an in-line mixer such as a static mixer from the viewpoint that the apparatus is simple. By providing the circulation path 2 with an in-line mixer, it is possible to efficiently mix carbon dioxide with other components in the flow path so as to obtain a uniform circulating fluid.

In addition, the circulation path 2 is preferably one in which a pressure control means 13 for controlling the opening degree of the circulation path 2 is provided in between the mixing means 9 and the gas-liquid separation means 11.

Examples of the pressure control means 13 may include a back pressure valve.

In addition, the circulation path 2 includes the gas-liquid separation means 11 for conducting the gas-liquid separation treatment by reducing the pressure of the circulating fluid containing carbon dioxide obtained by the mixing means 9.

By the gas-liquid separation means 11, the excess carbon dioxide gasified is separated, and as a result, the uneven flow of the circulating fluid due to the gasification is suppressed and the poor wetting of the heterogeneous catalyst in the reactor 1 can be eliminated, and thus it is possible to efficiently utilize the catalyst.

Examples of the gas-liquid separation means 11 may include a gas-liquid separation tank capable of storing a liquid while separating the supplied gas-liquid two-phase flow into a gas and a liquid. By using the gas-liquid separation tank, it is possible to establish the circulation between the reactor 1 and the circulation path 2 by guiding the circulating fluid to the gas-liquid separation tank and circulating this upon start of operation of the apparatus. In addition, it is possible to store the circulating fluid therein after the operation is completed as well.

In addition, the gas-liquid separation means 11 is provided with a gas discharge path for discharging the separated gas above the portion connected to the circulation path 2. In addition, the gas discharge path is provided with a pressure control means 14 for controlling the internal pressure of the gas-liquid separation means 11.

Examples of the pressure control means 14 may include a back pressure valve.

By adjusting the pressure control means 13 and 14, it is possible to apply a predetermined pressure difference between the gas-liquid separation means 11 and the mixing means 9 and to separate excess carbon dioxide through gasification.

In addition, the circulation path 2 is provided with the pressurization means 12 for pressurizing the circulating fluid subjected to the gas-liquid separation treatment by the gas-liquid separation means 11 to a predetermined pressure.

By the pressurization means 12, the circulating flow rate can be properly controlled and the pressure is increased to a predetermined pressure (substantially reaction pressure). By this, the circulating fluid is in a state of not substantially including a gas phase and it is possible to suppress the gasification of carbon dioxide in the reactor 1.

Examples of the pressurization means 12 may include a circulation pump.

In addition, in the circulation path 2, an epoxide inflow portion into which the epoxide supplied by the epoxide supply means 8 flows is preferably provided downstream of the gas liquid separation means 11 in order to prevent carbon dioxide gasified by the gas-liquid separation treatment from being entrained by the epoxide. It is more preferably provided at a position close to the reactor inlet in order to suppress a side reaction, and thus it is even more preferably provided in between the pressurization means 12 and the mixing means 10.

In addition, the circulation path 2 is preferably one that is provided with a heat exchange means 5.

The temperature at the reactor inlet 1*b* can be adjusted by the circulated ratio of cyclic carbonate/epoxide at the reactor inlet 1*b*, and the raw material fluid mixture passing through the reactor inlet 1*b* is preheated by the heat exchange means 5 and temperature at the reactor inlet 1*b* can be more easily adjusted. In addition, the heat exchange means 5 can be used in the case of preheating the inside of the system before start of the reaction (before introduction of epoxide).

The heat exchange means 5 may be one that can control the temperature by indirect heat exchange, and the operation is conducted at a high pressure, and thus a double tube heat exchanger having a simple structure and a corresponding heat exchange efficiency is preferable.

In addition, the heat exchange means 5 is preferably provided downstream of the gas-liquid separation tank 11 in order to suppress the vaporization of carbon dioxide by heating, although it may be provided at any place in the circulation path and the place is not particularly limited.

In addition, in the circulation path 2, the additive inflow portion into which, for example, the additive supplied by the additive supply means 7 flows may be at anyplace in the circulation path, and the place is not particularly limited. The supply amount of the additive is usually a small amount, and thus it is not required to prepare a separate mixing means when it is supplied upstream of the mixing means 10.

In addition, the circulation path 2 is provided with the mixing means 10 (the second mixing means) for mixing the epoxide supplied by the epoxide supply means 8 with the circulating fluid which flows into the circulation path 2 and is pressurized by the pressurization means 12 in the path.

By the mixing means 10, the supplied epoxide is uniformly mixed with other components.

As the mixing means 10, it is preferable to use an in-line mixer such as a static mixer from the viewpoint that the apparatus is simple. By providing the circulation path 2 with an in-line mixer, it is possible to efficiently mix the epoxide with other components in the flow path so as to obtain a uniform circulating fluid.

The circulating fluid that is homogeneously mixed by the mixing means 10 is supplied to the adiabatic reactor 1 filled with the catalyst through the reactor inlet 1b as a raw material fluid mixture, and as a result, carbon dioxide reacts with the epoxide in the reactor 1 to produce a cyclic carbonate.

The supply amount (circulating velocity) of the epoxide introduced into the reactor 1 is preferably from 0.001 to 10 kg/hr, more preferably from 0.01 to 1.0 kg/hr, even more preferably from 0.05 to 0.5 kg/hr with respect to 1 kg of the catalyst.

The content of carbon dioxide in the raw material fluid mixture introduced into the reactor 1 is preferably from 1 to 20, more preferably from 1.1 to 10, and even more preferably from 1.2 to 5 in terms of the ratio (molar ratio) of carbon dioxide/epoxide.

In addition, as the amount of the catalyst filled in the reactor 1, an arbitrary amount can be used in a range satisfying the above circulating velocity depending on the production quantity of a cyclic carbonate to be required.

In addition, the ratio (mass ratio) of carbon dioxide/epoxide circulated to the reactor 1 is preferably 1 or more, more preferably 10 or more, even more preferably 12.5 or more, and even more preferably 15 or more, and preferably 100 or less, more preferably 80 or less, even more preferably 60 or less, even more preferably 50 or less, even more preferably 40 or less, and even more preferably 30 or less. By adjusting the ratio, it is possible to adjust the temperature at the reactor inlet 1b.

In addition, the raw material fluid mixture does not substantially includes a gas phase, and thus it may be allowed to flow from the top to the bottom of the reactor 1 (down-flow system) or to flow from the bottom to the top of the reactor 1 (up-flow system). The up-flow system is preferable since the bubbles easily escape even in a case in which bubbles are accidentally generated.

The fluid mixture in a liquid form flowed out through the reactor outlet 1a mainly contains the cyclic carbonate produced in the reactor 1 and unreacted carbon dioxide, and it also contains the unreacted epoxide depending on the reaction conditions. A portion thereof is led to the circulation path 2 as described above, and the remainder discharged from the discharge path 3 may be sent to, for example, a separation and purification means (not illustrated).

The discharge path 3 is configured as an arbitrary proper pipe. The material constituting the pipe is not particularly limited, and it is preferably SUS from the viewpoint of excellent corrosion resistance.

In addition, the discharge path 3 is provided with a control valve 15. By the control valve 15, the liquid flow that is led to the circulation path 2 and circulated in the system and the liquid flow to be discharged from the discharge path 3 can be adjusted.

Second Embodiment

Next, the apparatus for producing a cyclic carbonate according to the second embodiment of the present invention (second producing apparatus) will be described. The description on the parts of the second producing apparatus which are the same as those of the first producing apparatus will be omitted.

The producing apparatus of the present embodiment includes a fixed bed multi-stage reactor in which two or more of the same adiabatic reactors as the reactor 1 are connected in series, and in the producing apparatus, the circulation path is provided such that at least a portion of the fluid mixture in a liquid form flowed out through the outlet of the last stage reactor included in the fixed bed multi-stage reactor is returned to the first stage reactor included in the fixed bed multi-stage reactor.

In the present invention, the amount of catalyst with respect to the production quantity of a cyclic carbonate is approximately constant regardless of the number of reactors. Hence, it is possible to enhance the production capacity by increasing the number of reactors in the producing apparatus of the present embodiment.

The producing apparatus of the present embodiment is preferably one that further includes an epoxide supply means for continuously supplying an epoxide in a liquid or solution form to at least one flow path among the flow paths for connecting the respective reactors included in the fixed bed multi-stage reactor and a mixing means for mixing the epoxide supplied by the epoxide supply means with the fluid mixture in a liquid form flowed into the flow path in the flow path.

By employing such a configuration, it is possible to supply the epoxide into a plurality of reactors in a divided manner and to suppress the catalyst deterioration by decreasing the amount of the epoxide to be supplied to the first stage reactor and the heat generation in the reactor. In addition, it is more preferable to employ such a configuration, since it is possible to distribute the heat generated by the reaction to all the reactors by continuously supplying the epoxide in a liquid or solution form to all the flow paths connecting the respective reactors, mixing it in all the flow paths connecting the respective reactors, and introducing the mixture into the inlet of the next stage reactor.

In addition, the producing apparatus of the present embodiment is preferably one in which at least one flow path among the flow paths for connecting the respective reactors included in the fixed bed multi-stage reactor includes a heat exchange means for removing heat from the fluid mixture in a liquid form flowed into the flow path by indirect heat exchange.

By employing such a configuration, it is possible to easily remove the reaction heat generated in the previous stage reactor and to easily control the temperature in the next stage reactor in a desired range (substantially the reaction temperature). In addition, it is more preferable to employ a configuration since it is possible to more efficiently conduct the heat removal by cooling all the flow paths connecting the respective reactors by indirect heat exchange and removing the reaction heat.

Figure 2:
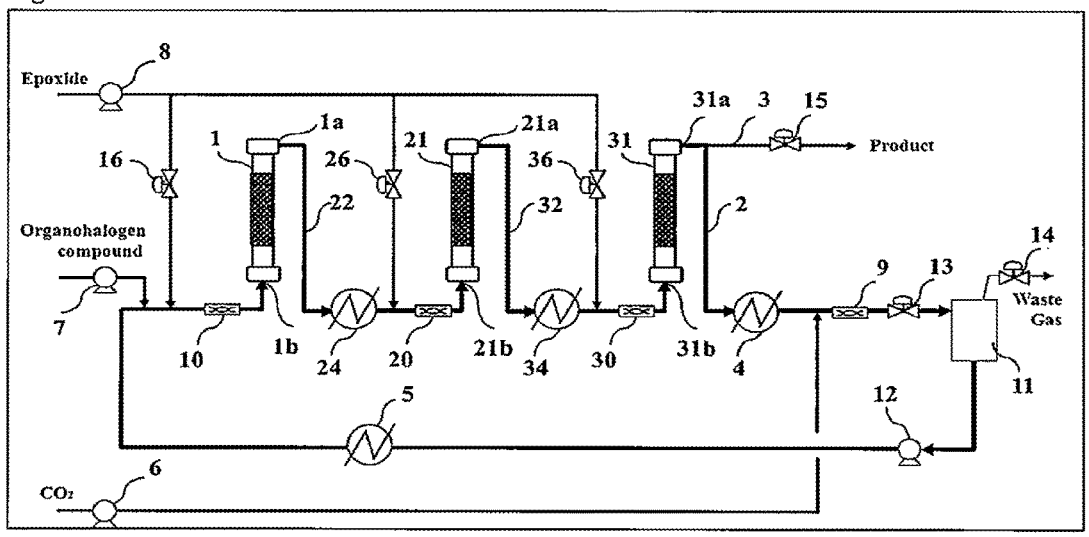
FIG. 2 is a diagram schematically illustrating an example of a second embodiment of the apparatus for producing a cyclic carbonate of the present invention.

FIG. 2 is a diagram schematically illustrating an example of the apparatus for producing a cyclic carbonate using a fixed bed multi-stage reactor according to the second embodiment of the present invention.

The apparatus for producing a cyclic carbonate illustrated in FIG. 2 includes a fixed bed multi-stage reactor in which three adiabatic reactors (reactor 1, reactor 21, and reactor 31) are connected in series, and the fixed bed multi-stage reactor is provided with a flow path 22 from an outlet 1a of the first stage reactor (reactor 1) to an inlet 21b of the second stage reactor (reactor 21) and a flow path 32 from a second stage reactor outlet 21a to an inlet 31b of the third stage reactor (reactor 31). A portion of the fluid mixture in a liquid form flowed out through the third stage reactor outlet 31a is led to a first stage reactor inlet 1b via the circulation path 2 in the same manner as the process illustrated in FIG. 1.

The flow path 22 and the flow path 32 are configured as an arbitrary proper pipe in the same manner as the circulation path 2. The material constituting the pipe is not particularly limited, and it is preferably SUS from the viewpoint of excellent corrosion resistance.

The reactor 21 and the reactor 31 may be those that are configured so as to be able to be filled with the heterogeneous catalyst for reacting an epoxide with carbon dioxide in the same manner as the reactor 1, and a tubular reactor is preferable. In addition, the material constituting the reactor 21 and the reactor 31 is not particularly limited, and it is preferably SUS from the viewpoint of excellent corrosion resistance. In addition, it is possible to greatly cut down the facility cost by using an inexpensive adiabatic reactor as the reactor 21 and the reactor 31.

In addition, for example, glass beads may be filled before or after the catalyst when the heterogeneous catalyst is filled in the reactor 21 and the reactor 31.

In addition, the apparatus for producing a cyclic carbonate illustrated in FIG. 2 includes an epoxide supply means 8 for continuously supplying an epoxide in a liquid or solution form in the same manner as the producing apparatus of the first embodiment. Furthermore, in the producing apparatus, control valves 16, 26, and 36 are also disposed to each of the flow path 22 and the flow path 32 in addition to the circulation path 2 so that the epoxide is supplied into the flow path.

By such a configuration, the epoxide as a reaction raw material is supplied to the fluid mixture in a liquid form to flow the circulation path 2, the flow path 22, and the flow path 32 in a state of being a liquid or solution.

In addition, it is possible to respectively control the supply amount of the epoxide supplied to the reactors 1, 21, and 31 by the control valves 16, 26, and 36.

Incidentally, an epoxide supply means may be individually disposed to the respective flow paths instead of disposing the control valves 16, 26, and 36. In this case, the supply amount of the epoxide to the respective reactors can be respectively controlled by the individual epoxide supply means.

In addition, the flow paths 22 and 32 are respectively provided with heat exchange means 24 and 34 for removing heat from the fluid mixture in a liquid form flowed into the flow path by indirect heat exchange.

By providing the flow paths 22 and 32 with the heat exchange means 24 and 34, it is possible to easily remove the reaction heat generated in the previous stage reactor and to easily control the temperature in the next stage reactor in a desired range (substantially the reaction temperature).

As the heat exchange means 24 and 34, an arbitrary heat exchanger 4 can be used as long as it can remove the reaction heat by lowering the temperature of the circulating fluid in a liquid form passing through the means. Specific examples thereof may include a multi-tubular cylindrical heat exchanger, a double tube heat exchanger, a plate heat exchanger, an air cooler, an irrigation cooler, a coil heat exchanger, and a scroll heat exchanger, and the circulating flow rate is relatively a small flow rate and the operation is conducted at a high pressure, and thus a double tube heat exchanger, an air cooler, and an irrigation cooler are particularly proper and preferable. In addition, the overall heat transfer coefficient of these heat exchangers is preferably about 200 kcal/($m^2$ hrK) or more.

In addition, the flow paths 22 and 32 respectively include mixing means 20 and 30. By the mixing means 20 and 30, the supplied epoxide is mixed with the fluid mixture in a liquid form flowed into the flow path in the flow path.

As the mixing means 20 and 30, it is preferable to use an in-line mixer such as a static mixer from the viewpoint that the apparatus is simple.

In addition, in the apparatus for producing a cyclic carbonate illustrated in FIG. 2, the heat exchange means 24 in the flow path 22, the epoxide inflow portion, and the mixing means 20 are provide from the outlet 1a of the first stage reactor toward the inlet 21b of the second stage reactor in the order of the heat exchange means 24, the epoxide inflow portion, and the mixing means 20. In addition, the heat exchange means 34 in the flow path 32, the epoxide inflow portion, and the mixing means 30 are provided from the outlet 21a of the second stage reactor toward the inlet 31b of the third stage reactor in the order of the heat exchange means 34, the epoxide inflow portion, and the mixing means 30.

It is possible to efficiently remove heat from the fluid mixture in a liquid form, to uniformly and efficiently mix it with the epoxide, and to supply the mixture to the next reactor as these are provided in such an order.

In addition, by such a configuration, it is possible to increase the temperature difference between the outlet temperature and the inlet temperature in the respective reactors within a range in which the catalyst deterioration does not occur and to efficiently conduct the reaction at a high reaction rate in all the reactors.

In addition, the producing apparatus of the present embodiment is not limited to the producing apparatus illustrated in FIG. 2. In FIG. 2, a producing apparatus using a fixed bed multi-stage reactor in which three adiabatic reactors 1, 21, and are 31 connected in series is illustrated, while the number of adiabatic reactors may be two or more. The number of adiabatic reactors included in the fixed bed multi-stage reactor is preferably from 2 to 10, more preferably from 2 to 6, and even more preferably from 2 to 4.

In addition, it is possible to provide the multi-stage adiabatic reactor with a flow path for bypassing the respective reactors, and this makes it possible to appropriately adjust the production quantity and further to switch the catalyst while continuing the production.

Furthermore, by appropriately changing the flow path between the respective reactors, it is also possible to switch the connection order of the reactors and to conduct the reaction in an optimized order depending on the deterioration status of the catalyst.

Incidentally, the supply amount of the epoxide to be introduced into the respective adiabatic reactors, the content of carbon dioxide in the raw material fluid mixture, the amount of the catalyst to be filled in the respective adiabatic reactors, and the ratio (mass ratio) of cyclic carbonate/epoxide to be circulated to the respective adiabatic reactors are the same as those in the first embodiment.

[(2) Method for Producing Cyclic Carbonate]

Next, the method for producing a cyclic carbonate of the present invention will be described.

The method for producing a cyclic carbonate of the present invention can be performed by using the producing apparatus of the present invention such as the first producing apparatus or second producing apparatus described above. In addition, the method is performed by continuously supplying a raw material fluid mixture containing an epoxide and carbon dioxide to an adiabatic reactor filled with a heterogeneous catalyst, circulating at least a portion of a fluid mixture in a liquid form flowed out through a reactor outlet (the last stage reactor outlet in the case of a fixed bed multi-stage reactor) to a circulation path to return to the reactor, removing the reaction heat in the circulation path, continuously supplying the epoxide and carbon dioxide to the circulating fluid, and mixing them in a flow path.

The inlet temperature (reaction temperature) of the adiabatic reactor (it refers to the respective adiabatic reactors included in the multi-stage reactor in the case of using a fixed bed multi-stage reactor. The same applies hereinafter for the description of the temperature) is preferably 60° C. or higher, more preferably 70° C. or higher, even more preferably 80° C. or higher, even more preferably 90° C. or higher, even more preferably 100° C. or higher, and even more preferably 110° C. or higher from the viewpoint of the reaction rate and the reaction efficiency, and it is preferably at 160° C. or lower, more preferably 150° C. or lower, even more preferably 140° C. or lower, even more preferably 130° C. or lower, and even more preferably 120° C. or lower from the viewpoint of suppressing the thermal decomposition and preventing the deactivation of the catalyst lifetime.

In addition, the temperature at the outlet of the adiabatic reactor is preferably 80° C. or higher, more preferably 90° C. or higher, and even more preferably 100° C. or higher, and it is preferably 180° C. or lower, more preferably 160° C. or lower, and even more preferably 140° C. or lower.

The temperature difference between the outlet temperature and inlet temperature in the reactor is preferably 10° C. or more, more preferably 20° C. or more, and even more preferably 30° C. or more, and it is preferably 80° C. or less, more preferably 70° C. or less, even more preferably 60° C. or less, and even more preferably 50° C. or less. In addition, it is preferable to be outlet temperature>inlet temperature.

Incidentally, the quantity of heat generated per production quantity is constant (reaction heat of about 100 kJ/mol, for example, in the case of synthesizing ethylene carbonate from ethylene oxide and carbon dioxide), and thus the inlet temperature in the adiabatic reactor and the temperature difference can be adjusted by the flow ratio of the cyclic carbonate to be circulated to the epoxide.

In addition, the reaction pressure is preferably from 1 to 15 MPa from the viewpoint of preventing the gasification of carbon dioxide and epoxide and using an economical facility. Furthermore, it is preferable to conduct the reaction in the vicinity of the critical pressure (7.38 MPa) of carbon dioxide from the viewpoint of the yield of a cyclic carbonate, and it is more preferable to conduct the reaction at a pressure above the critical pressure in order to suppress the uneven flow in the reactor due to the gasification of carbon dioxide. Specifically, it is preferable to conduct the reaction at from 7 to 10 MPa and it is more preferable to conduct the reaction at from 7.4 to 9 MPa.

Hereinafter, the method for producing a cyclic carbonate of the present invention will be specifically described with reference to FIG. 1 and taking a case of using the apparatus for producing a cyclic carbonate according to the first embodiment of the present invention as an example.

The producing method of the present invention is preferably a method to first establish the circulation between the reactor 1 and the circulation path 2 by circulating a cyclic carbonate to the producing apparatus of the present invention described above prior to the supply of carbon dioxide and an epoxide. As the cyclic carbonate, it is possible to use a cyclic carbonate produced from the circulating fluid (for example, circulating fluid after gas-liquid separation) of the previous lot or by the method of the present invention, or a commercially available cyclic carbonate may be used.

Specific examples of the method for establishing the circulation may include a method in which a cyclic carbonate that is heated in advance is guided to the gas-liquid separation means 11 and this is sent and circulated to the heat exchange means 5, the reactor 1, the circulation path 2, and the heat exchange means 4 by the pressurization means 12. In addition, the circulating fluid of the previous lot is stored in the gas-liquid separation means 11 and this may be used. In both cases, it is preferable to adjust the temperature at the reactor inlet by the heat exchange means 5.

Subsequently, carbon dioxide is supplied into the circulation path 2 while controlling the supply amount thereof by the carbon dioxide supply means 6. Carbon dioxide is stirred by the mixing means 9 and circulated in the process in a state of being completely mixed with, namely, completely dissolved in the cyclic carbonate.

Surplus carbon dioxide that is not dissolved in the cyclic carbonate is separated by the gas-liquid separation means 11.

Surplus carbon dioxide is evacuated through the top of the gas-liquid separation means 11, while the pressure of the gas-liquid separation means 11 is controlled to a pressure lower than the pressure of the reactor 1 (thus, the pressure of the mixing means 9) by this excess gas and the pressure control means 14. The pressure difference between the gas-liquid separation means 11 and the reactor 1 is preferably 0.1 MPa or more, more preferably 0.3 MPa or more, even more preferably 0.5 MPa or more, and even more preferably 1.0 MPa or less.

By separating the excess gas at a pressure lower than the pressure of the reactor 1, it is possible to supply carbon dioxide that is dissolved in the cyclic carbonate and hardly gasified to the reactor 1, and the uneven flow in the reactor 1 is prevented.

Subsequently, the circulating liquid after the gas-liquid separation is pressurized to a desired pressure (substantially the reaction pressure), and the epoxide and the additive if necessary are supplied. The epoxide is supplied into the circulation path while controlling the supply amount thereof by the epoxide supply means 8 and stirred by the mixing means 10, whereby a uniform raw material fluid mixture is formed.

The additive is supplied into the circulation path while controlling the supply amount thereof by the additive supply means 7. The supply location of the additive is not particularly limited, and the supply amount of the additive is usually a small amount, and thus it is not required to prepare a separate mixing means when it is supplied upstream of the mixing means 10.

The raw material fluid mixture containing an epoxide is supplied to the reactor 1 and brought into contact with the catalyst filled in the reactor 1 so that the continuous production is started.

Incidentally, a fixed bed multi-stage reactor in which a plurality of adiabatic reactors are connected in series may be used as the reactor as described in the second embodiment. In the case of increasing the number of adiabatic reactors, at least a portion of the fluid mixture in a liquid form flowed out through the last stage reactor outlet is led to the circulation path 2 to return to the first stage reactor inlet.

At this time, it is preferable to continuously supply an epoxide in a liquid or solution form to at least one flow path among the flow paths connecting the respective reactors included in the fixed bed multi-stage reactor and to mix the epoxide supplied in the epoxide supply step with the fluid mixture in a liquid form flowed into the flow path in the flow path. Furthermore, it is more preferable that an epoxide in a liquid or solution form is continuously supplied to all the flow paths connecting the respective reactors, mixed in all the connecting flow paths for connecting the respective reactors, and introduced into the inlet of the next stage reactor.

In addition, it is preferable to remove heat from the fluid mixture in a liquid form flowed into at least one flow path among the flow paths connecting the respective reactors included in the fixed bed multi-stage reactor by indirect heat exchange, and it is more preferable to cool the fluid mixture in a liquid form in all the flow paths connecting the respective reactors by indirect heat exchange to remove the reaction heat.

The fluid mixture in a liquid form flowed out through the reactor outlet 1a (the last stage reactor outlet in the case of a multi-stage reactor) mainly contains the cyclic carbonate produced in the reactor and unreacted carbon dioxide, and it contains the unreacted epoxide depending on the reaction conditions. A portion thereof is led to the circulation path 2 as described above and cooled by the heat exchange means 4 to remove the reaction heat.

The remainder is sent from the discharge path 3 to the next step (separation and purification step) if necessary. The discharge quantity from the discharge path 3 is adjusted by the control valve 15 such that the amount of circulating fluid in the system is constant.

As the separation and purification step, it is possible to apply, for example, a step of separating carbon dioxide and the epoxide by depressurizing the fluid mixture in a liquid form and recycling carbon dioxide by compressing the discharged gas and a step of purifying the crude cyclic carbonate after the removal of carbon dioxide and epoxide by the methods such as distillation, crystallization, and adsorption.

EXAMPLES

Hereinafter, the present invention will be described in detail with reference to Examples, but the present invention is not limited to these Examples. Incidentally, the analysis methods used in Examples are as follows.

(1) X-Ray Fluorescence Analysis

X-ray fluorescence analysis was used for the measurement of the bromine- and phosphorus-modified amount of the catalyst. The analysis conditions were as follows.

Apparatus: product name "System3270" (manufactured by Rigaku Corporation)
Measurement conditions: Rh tube, tube voltage: 50 kV, tube current: 50 mV, and vacuum atmosphere, and detector: SC and F-PC (2) Thermogravimetric Measurement A differential thermogravimetric simultaneous measurement apparatus was used for the thermogravimetric measurement of the catalyst. The analysis conditions were as follows.

Apparatus: instrument name "TG-DTA6200" (manufactured by Hitachi High-Tech Science Corporation)
Sample amount: 14 mg (the sample ground with a mortar was weighed on an aluminum pan)
Measurement range and raised temperature: room temperature (25° C.)→raised at 5° C./min→kept at 50° C. for 3 hours→raised at 0.5° C./min→kept at 250° C. for 3 hours
Atmosphere: 50 mL/min in nitrogen stream (3) Gas Chromatography Gas chromatography was used for the composition analysis of the reaction solution. The analysis conditions were as follows.

Apparatus: product name "GC-2010Plus" (manufactured by Shimadzu Corporation)
Detector: FID
INJ temperature: 150° C.
DET temperature: 260° C.
Sample volume: 0.3 µL
Split ratio: 5
Column: DB-624 (60 m, 0.32 mm ID, 1.8 µm, manufactured by Agilent Technologies)
Column temperature conditions: kept at 70° C. for 3 minutes→raised at 5° C./min→120° C.→raised at 10° C./min→kept at 250° C. for 5 minutes (31 minutes in total)

Catalyst Synthesis Example 1: Synthesis of Silica Gel Catalyst Having Surface Modified with Tributyl Phosphonium Bromide Into a 200 L SUS reaction tank, 40 kg of silica gel having a form of bead (CARiACT Q-10 (average pore size: 10 nm, particle size: 1.2 to 2.4 mm, specific surface area: 300 m$^2$/g) manufactured by FUJI SILYSIA CHEMICAL LTD) and 100 L of xylene were introduced. The azeotropic dehydration of xylene-water was conducted for 2 hours while refluxing at 140° C. to remove moisture contained in the silica gel. Subsequently, the reaction tank was purged with nitrogen, and 4.4 kg of 3-bromopropyltrimethoxysilane was added thereto dropwise. This was heated and refluxed for 9 hours at 135° as it was to conduct the silanizing reaction. The reaction product thus obtained was withdrawn from the reaction tank, the catalyst precursor (bromopropylated silica gel) in the reaction product was separated by filtration and then washed with 40 L of xylene. The bromine-modified amount in the catalyst precursor obtained here was 0.39 mmol/g.

Subsequently, the catalyst precursor thus obtained and 100 L of xylene were introduced into the reaction tank, the reaction tank was purged with nitrogen, and then 9.1 kg of tri-n-butyl phosphine was added thereto dropwise. This was heated for 24 hours while refluxing as it was to conduct the reaction modifying with quaternary phosphonium.

After the reaction, the reaction product was separated by filtration and washed 6 times with 40 L of acetone. Thereafter, the reaction product was dried for the night at 120° C. in a nitrogen stream under reduced pressure, thereby obtaining 46 kg of the desired silica gel having the surface modified with tributylphosphonium bromide. The amount of bromine-modified amount in the catalyst was 0.32 mmol/g, and the phosphorus-modified amount in the catalyst was 0.33 mmol/g.

Reference Example 1: Thermogravimetric Measurement of Catalyst

The thermogravimetric measurement of the catalyst obtained in Catalyst Synthesis Example 1 was conducted. The results are illustrated in FIG. 3.

Figure 3:
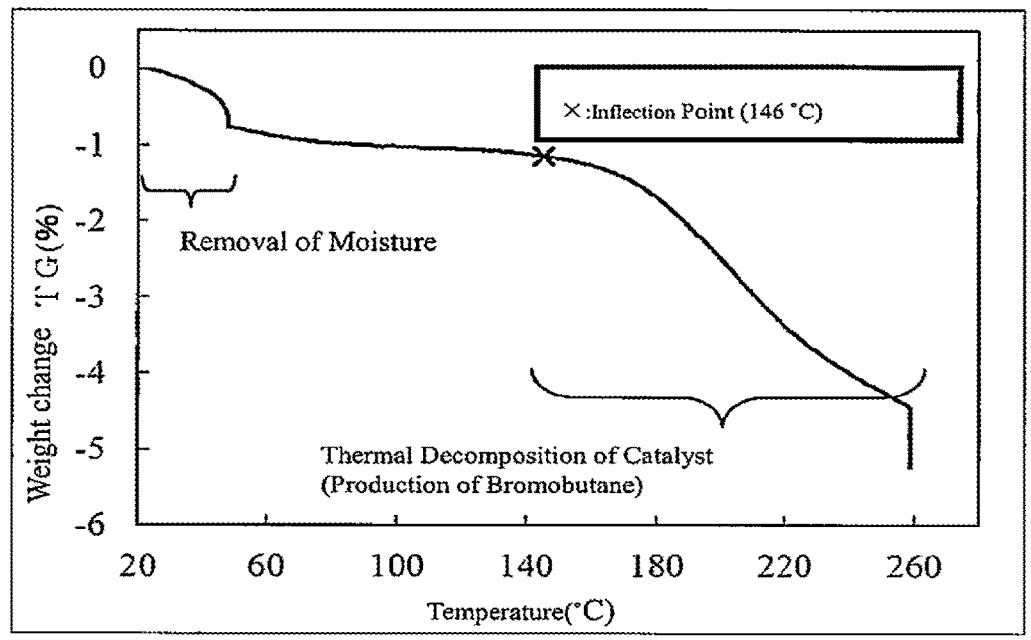
FIG. 3 is a diagram illustrating the results of thermogravimetric measurement of the catalyst.

As illustrated in FIG. 3, the thermal decomposition of the catalyst started to be observed at the temperature of 146° C. or higher, and 1-bromobutane was detected as the decomposition product. From this result, the upper limit temperature in the reactor was set to 140° C. in the following Examples.

Reference Example 2: Discussion on Effect of Reaction Pressure to Yield of Ethylene Carbonate Into a 50 mL autoclave equipped with a stirrer, 400 mg of the catalyst obtained in Catalyst Synthesis Example 1 was introduced and dried for 1 hour at 120° C. under reduced pressure. The inside of the autoclave was filled with nitrogen to the atmospheric pressure and cooled to room temperature, 4 mL (60 mmol) of ethylene oxide was then introduced thereinto. Subsequently, the autoclave was temporarily filled with carbon dioxide to 1.5 MPaG, the inside of the autoclave was then heated to 100° C. while being stirred at 800 rpm by the stirrer, the autoclave was further filled with carbon dioxide to adjust the internal pressure in the range of from 3.0 to 18.3 MPa, and the reaction was conducted for 1 hour. After the reaction was completed, cooling was conducted, and remained carbon dioxide was released to depressurize the inside of the autoclave. The reaction solution thus obtained was analyzed by gas chromatography to determine the yield of ethylene carbonate. The results are illustrated in FIG. 4.

Figure 4:
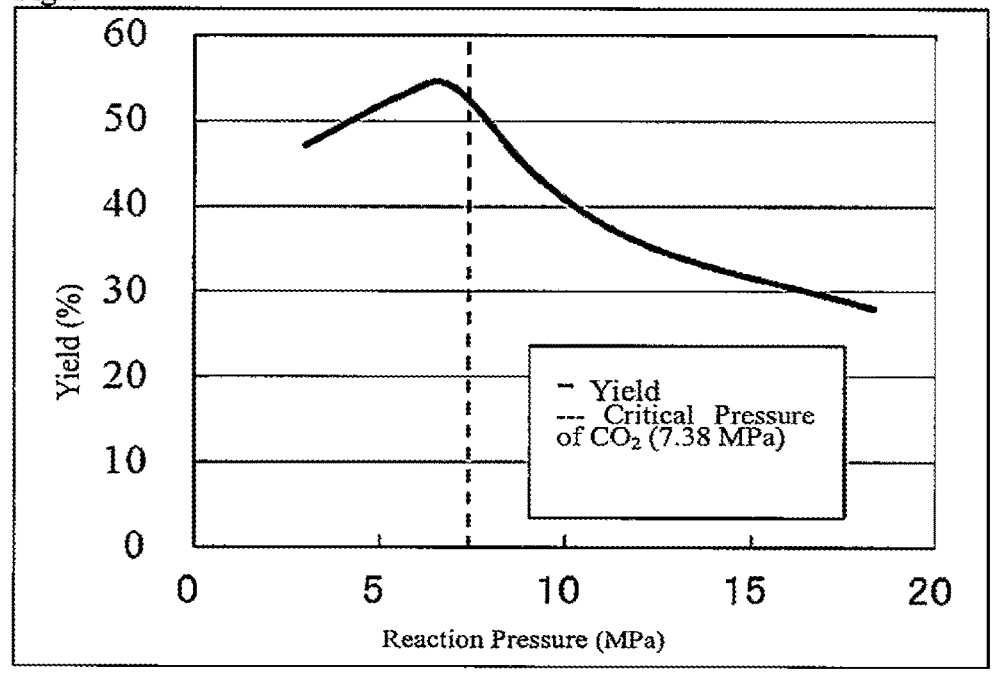
FIG. 4 is a diagram illustrating the effect of reaction pressure to yield of ethylene carbonate.

As illustrated in FIG. 4, it has been indicated that the relation between the reaction pressure and the yield of ethylene carbonate is a convex relation to have the peak in the vicinity of the critical pressure of carbon dioxide. The reaction pressure was set to 8 MPa in the following Examples from the viewpoint of this result and suppressing the gasification of carbon dioxide.

Example 1: Production of Ethylene Carbonate Using Continuous Producing Apparatus The production of ethylene carbonate was conducted by using an apparatus that was respectively equipped with a double tube heat exchanger as the heat exchange means 4 and 5, a pump as the supply means 6, 7, and 8 of, for example, a raw material and the pressurization means 12, a static mixer as the mixing means 9 and 10, a gas-liquid separation tank as the gas-liquid separation means 11, and a back pressure valve as the pressure control means 13 and 14 in the apparatus illustrated in FIG. 1.

A reactor 1 having an inner diameter of 50 mm, a length of 100 cm, and a volume of 2000 mL was filled with 530 g (1000 mL) of the catalyst obtained in Catalyst Synthesis Example 1 and further filled with 1560 g (1000 mL) glass beads in total having a particle size of 4 mm before and after the catalyst.

Subsequently, 5.0 kg of ethylene carbonate that was dissolved by heating in advance was initially guided to the gas-liquid separation tank 11, and this was sent and circulated to the heat exchanger 5, the static mixer 10, the reactor 1, the circulation path 2, the heat exchanger 4, and the static mixer 9 at a flow rate of 2050 g/hr by the pump 12. At that time, the temperature at the reactor inlet was adjusted to 100° C. by the heat exchanger 5.

Subsequently, carbon dioxide was supplied at a flow rate of 53 g/hr by the pump 6. At that time, the carbon dioxide was circulated in a state of being completely mixed with, namely, completely dissolved in ethylene carbonate by being stirred by the static mixer 9. The excess carbon dioxide that is not dissolved in ethylene carbonate is separated by the gas-liquid separation tank 11 and thus the uneven flow is prevented in the reactor 1. The excess carbon dioxide was discharged from the top of the gas-liquid separation tank 11, and the pressure of the gas-liquid separation tank 11 was kept at 7.5 MPaG by this excess gas and the back pressure valve 14.

Subsequently, the pressure in the reactor 1 was adjusted to 8.0 MPaG by the back pressure valve 13. In this manner, the pressure difference between the static mixer 9 and the reactor 1 and the gas-liquid separation tank 11 was set to 0.5 MPa. In addition, the pressure of the liquid after the gas-liquid separation was increased to 8.0 MPaG by the pump 12, and the liquid was supplied to the reactor 1. By this operation, carbon dioxide that was completely dissolved in ethylene carbonate and hardly gasified was supplied to the reactor 1.

Incidentally, the saturated solubility of carbon dioxide in ethylene carbonate is about 12% by mass under the condition (8 MPa and 100° C.) at the reactor inlet 1b, and thus the solubility of carbon dioxide in the circulating fluid after the gas-liquid separation was about 11% by mass.

Subsequently, 2-bromoethanol as an additive for performance maintenance of the catalyst was supplied to the reactor 1 at a flow rate of 0.035 g/hr by the pump 7, and ethylene oxide was supplied to the reactor 1 at a flow rate of 44 g/hr by the pump 8, thereby starting the continuous production (ratio (mass ratio) of cyclic carbonate/epoxide circulated to the reactor 1=40). Incidentally, 2-bromoethanol and ethylene oxide were mixed with ethylene carbonate by the static mixer 10 and supplied to the reactor 1.

The opening degree of the control valve 15 was adjusted so that the liquid level in the gas-liquid separation tank 11, namely, the amount of circulating fluid in the system was constant, and ethylene carbonate thus produced was withdrawn through the discharge path 3. The flow rate of withdrawn ethylene carbonate was about 88 g/hr.

In addition, ethylene oxide was not detected in the gas discharged from the top of the gas-liquid separation tank 11, and thus the conversion ratio of ethylene oxide was calculated by the following equation.

Conversion ratio $X=\{$(flow rate of supplied ethylene oxide)−(flow rate of withdrawn ethylene oxide)$\}/$(flow rate of supplied ethylene oxide)×100.

The concentration of ethylene oxide in the withdrawn ethylene carbonate was 0.29%, and the conversion ratio of ethylene oxide was calculated to be 99.4%.

In addition, while the reaction was continued for 260 hours, the temperature at the reactor outlet was maintained in a range of from 115 to 118° C. and a decrease in conversion ratio due to the catalyst deactivation was not also observed. In other words, it has been demonstrated that the temperature in the reactor is properly controlled by indirect heat exchange and the catalytic performance can be maintained even during a long-term operation.

Example 2: Simulation by One Reactor

The relation among the reactor temperature, the amount of ethylene carbonate circulated, and the amount of catalyst was simulated under the following conditions in the embodiment illustrated in FIG. 1. The results are presented in Table 1.

Simulation Software: PRO II (developed by Invensys Process Systems (S) Pte Ltd) physical properties estimation method SRK-M Apparatus: apparatus that was respectively equipped with a double tube heat exchanger as the heat exchange means 4 and 5, a pump as the supply means 6, 7, and 8 of, for example, a raw material and the pressurization means 12, a static mixer as the mixing means 9 and 10, a gas-liquid separation tank as the gas-liquid separation means 11, and a back pressure valve as the pressure control means 13 and 14 in the apparatus illustrated in FIG. 1

Production quantity of ethylene carbonate per year (8000 hours): 1,000 tons

Supply amount of ethylene oxide (pump 6): 63 kg/hr
Supply amount of 2-bromo-ethanol (pump 7): 0.05 kg/hr
Supply amount of carbon dioxide (pump 6): 63 kg/hr Conversion ratio of ethylene oxide: 99%

Number of reactors: 1

Pressure in reactor: 8 MPa

Temperature at adiabatic reactor inlet: 60° C., 70° C., 80° C., 90° C., 100° C., 110° C., 120° C., 130° C., and 135° C.

Upper limit temperature in adiabatic reactor (temperature at adiabatic reactor outlet): 140° C.

ΔT: temperature difference between reactor outlet 1a and reactor inlet 1b

EC/EO circulation and dilution ratio: obtained by dividing flow rate of ethylene carbonate at reactor inlet 1b by supply amount of ethylene oxide (63 kg/hr)

Example 3: Simulation by Three Reactors

The relation among the reactor temperature, the amount of ethylene carbonate circulated, and the amount of catalyst was simulated under the following conditions in the embodiment illustrated in FIG. 2. The results are presented in Table 1.

Simulation Software: PRO II (developed by Invensys Process Systems (S) Pte Ltd) physical properties estimation method SRK-M Apparatus: apparatus that was respectively equipped with a double tube heat exchanger as the heat exchange means 4, 5, 24, and 34, a pump as the supply means 6, 7, and 8 of, for example, a raw material and the pressurization means 12, a static mixer as the mixing means 9, 10, 20, and 30, a gas-liquid separation tank as the gas-liquid separation means 11, and a back pressure valve as the pressure control means 13 and 14 in the apparatus illustrated in FIG. 2

Production quantity of ethylene carbonate per year (8000 hours): 1,000 tons

Supply amount of ethylene oxide (control valve 16): 21 kg/hr (control valve 26): 21 kg/hr (control valve 36): 21 kg/hr Supply amount of 2-bromo-ethanol (pump 7): 0.05 kg/hr Supply amount of carbon dioxide (pump 6): 64 kg/hr Conversion ratio of ethylene oxide: 99%

Number of reactors: 3

Pressure in reactor: 8 MPa

Temperature at adiabatic reactor inlet: 110° C., 120° C., 130° C., and 135° C.

Upper limit temperature in adiabatic reactor (temperature at adiabatic reactor outlet): 140° C.

ΔT: temperature difference between reactor outlet 1a and reactor inlet 1b

EC/EO circulation and dilution ratio: obtained by dividing flow rate of ethylene carbonate at reactor inlet 1b by sum of supply amount of ethylene oxide (63 kg/hr)

Example 4: Simulation by Two Reactors

The reactor simulation was conducted in an embodiment in which the number of reactors was two, namely, the control valve 36, the flow path 32, the reactor 31, the heat exchange means 34, and the mixing means 30 were detached in the embodiment illustrated in FIG. 2.

Specifically, the relation among the reactor temperature, the amount of ethylene carbonate circulated, and the amount of catalyst was simulated under the following conditions. The results are presented in Table 1.

Simulation Software: PRO II (developed by Invensys Process Systems (S) Pte Ltd) physical properties estimation method SRK-M Apparatus: apparatus that was prepared by detaching the control valve 36, the flow path 32, the reactor 31, the double tube heat exchange means 34, and the static mixer 30 in the apparatus of Example 2

Production quantity of ethylene carbonate per year (8000 hours): 1,000 tons

Supply amount of ethylene oxide (control valve 16): 31.5 kg/hr (control valve 26): 31.5 kg/hr Supply amount of 2-bromo-ethanol (pump 7): 0.05 kg/hr Supply amount of carbon dioxide (pump 6): 64 kg/hr Conversion ratio of ethylene oxide: 99%

Number of reactors: 2

Pressure in reactor: 8 MPa

Temperature at adiabatic reactor inlet: 90° C., 100° C., 110° C., 120° C., 130° C., and 135° C.

Upper limit temperature in adiabatic reactor (temperature at adiabatic reactor outlet): 140° C.

ΔT: temperature difference between reactor outlet 1a and reactor inlet 1b

EC/EO circulation and dilution ratio: obtained by dividing flow rate of ethylene carbonate at reactor inlet 1b by sum of supply amount of ethylene oxide (63 kg/hr)

TABLE 1

| | | Temperature in reactor | | | Required circulation and dilution ratio | Required amount of catalyst | |
|---|---|---|---|---|---|---|---|
| | Number of reactors | Inlet (° C.) | Outlet (° C.) | ΔT (° C.) | EC/EO[*1] (wt/wt) | Per one reactor (L) | Total amount (L) |
| Example 2 | 1 | 60 | 140 | 80 | 10 | 590 | 590 |
| | 1 | 70 | 140 | 70 | 11 | 486 | 486 |
| | 1 | 80 | 140 | 60 | 13 | 442 | 442 |
| | 1 | 90 | 140 | 50 | 16 | 417 | 417 |
| | 1 | 100 | 140 | 40 | 20 | 401 | 401 |
| | 1 | 110 | 140 | 30 | 26 | 404 | 404 |
| | 1 | 120 | 140 | 20 | 39 | 449 | 449 |
| | 1 | 130 | 140 | 10 | 77 | 551 | 551 |
| | 1 | 135 | 140 | 5 | 153 | 671 | 671 |
| Example 3 | 3 | 110 | 140 | 30 | 9 | 138 | 415 |
| | 3 | 120 | 140 | 20 | 13 | 152 | 457 |
| | 3 | 130 | 140 | 10 | 26 | 185 | 555 |
| | 3 | 135 | 140 | 5 | 51 | 226 | 679 |
| Example 4 | 2 | 90 | 140 | 50 | 8 | 217 | 433 |
| | 2 | 100 | 140 | 40 | 10 | 206 | 411 |
| | 2 | 110 | 140 | 30 | 13 | 212 | 424 |

TABLE 1-continued

|  | Temperature in reactor | | | Required circulation and dilution ratio | Required amount of catalyst | |
|---|---|---|---|---|---|---|
| Number of reactors | Inlet (° C.) | Outlet (° C.) | ΔT (° C.) | EC/EO[*1] (wt/wt) | Per one reactor (L) | Total amount (L) |
| 2 | 120 | 140 | 20 | 20 | 231 | 461 |
| 2 | 130 | 140 | 10 | 40 | 286 | 572 |
| 2 | 135 | 140 | 5 | 78 | 344 | 688 |

[*1]ethylene carbonate/ethylene oxide

As presented in Table 1, the inlet temperature can be controlled by the circulated ratio of ethylene carbonate/ethylene oxide at the reactor inlet, and it is possible to conduct the reaction with a relatively small amount of catalyst of about from 400 to 500 L with respect to 1,000 tons/year of the production quantity of ethylene carbonate by optimizing these. Hence, it is possible to conduct the reaction in a compact reactor and to cut down the facility cost.

In addition, in the present invention, the amount of catalyst with respect to the production quantity of a cyclic carbonate is approximately constant regardless of the number of reactors, thus it is only required to sequentially increase the number of reactors, heat exchangers, and static mixers in the case of enhancing the production capacity, and economically excellent enhancement of production capacity is possible. Therefore, the disposal of facility is not required, and a double investment in facility is not required.

REFERENCE SIGNS LIST 1, 21, and 31: Reactor
1a, 21a, and 31a: Reactor outlet
1b, 21b, and 31b: Reactor inlet
2: Circulation path
3: Discharge path
4, 5, 24, and 34: Heat exchange means
6: Carbon dioxide supply means
7: Additive supply means
8: Epoxide supply means
9, 10, 20, and 30: Mixing means
11: Gas-liquid separation means
12: Pressurization means
13 and 14: Pressure control means
15, 16, 26, and 36: Control valve
22 and 32: Flow path between reactors

The invention claimed is:

1. An apparatus for producing a cyclic carbonate, the apparatus comprising:
an adiabatic reactor to be filled with a solid catalyst having an ionic organic compound immobilized on a support as a heterogeneous catalyst for reacting an epoxide with carbon dioxide;
a circulation path for returning at least a portion of a fluid mixture in a liquid form flowed out through a reactor outlet into the reactor;
a carbon dioxide supplier for continuously supplying carbon dioxide in a liquid form or a supercritical state into the circulation path; and
a first epoxide supplier for continuously supplying an epoxide in a liquid or solution form into the circulation path,
wherein the circulation path comprises
a circulation fluid heat exchanger for removing heat from a circulating fluid by indirect heat exchange,
a carbon dioxide mixer for mixing carbon dioxide supplied by the carbon dioxide supplier with the circulating fluid in a path,
a gas-liquid separator for conducting a gas-liquid separation treatment by reducing the pressure of a circulating fluid containing carbon dioxide obtained by the carbon dioxide mixer,
a pressurizer for pressurizing a circulating fluid after the gas-liquid separation treatment to a predetermined pressure, and
a first epoxide mixer for mixing the epoxide supplied by the first epoxide supplier with the circulating fluid in a path.

2. The apparatus according to claim 1, wherein:
the reactor is configured as a fixed bed multi-stage reactor by two or more adiabatic reactors connected in series; and
the circulation path is provided so as to return at least a portion of a fluid mixture in a liquid form flowed out through an outlet of a last stage reactor to a first stage reactor.

3. The apparatus according to claim 2, further comprising:
a second epoxide supplier for continuously supplying an epoxide in a liquid or solution form to at least one flow path among flow paths for connecting respective reactors included in the fixed bed multi-stage reactor; and
a second epoxide mixer for mixing the epoxide supplied by the second epoxide supplier with a fluid mixture in a liquid form flowed into a flow path in the flow path.

4. The apparatus according to claim 3, wherein at least one flow path among flow paths for connecting the respective reactors included in the fixed bed multi-stage reactor includes a fluid mixture heat exchanger for removing heat from a fluid mixture in a liquid form flowed into the flow path by indirect heat exchange.

5. The apparatus according to claim 4, wherein the carbon dioxide mixer and the first epoxide mixer are in-line mixers.

6. The apparatus according to claim 3, wherein the carbon dioxide mixer, the first epoxide mixer, and the second epoxide mixer are in-line mixers.

7. The apparatus according to claim 2, wherein at least one flow path among flow paths for connecting respective reactors included in the fixed bed multi-stage reactor includes a fluid mixture heat exchanger for removing heat from a fluid mixture in a liquid form flowed into the flow path by indirect heat exchange.

8. The apparatus according to claim 7, wherein the carbon dioxide mixer and the first epoxide mixer are in-line mixers.

9. The apparatus according to claim 2, wherein the carbon dioxide mixer and the first epoxide mixer are in-line mixers.

10. The apparatus according to claim 1, wherein the carbon dioxide mixer and the first epoxide mixer are in-line mixers.

11. A method for producing a cyclic carbonate by continuously supplying a raw material fluid mixture containing an epoxide and carbon dioxide to an adiabatic reactor filled with a solid catalyst having an ionic organic compound immobilized on a support as a heterogeneous catalyst and leading at least a portion of a fluid mixture in a liquid form flowed out through a reactor outlet to a circulation path to return to the reactor, the method comprising:
   removing heat from a circulating fluid by indirect heat exchange;
   continuously supplying carbon dioxide in a liquid form or a supercritical state into the circulation path;
   mixing carbon dioxide supplied in the carbon dioxide supply step with the circulating fluid in a path;
   reducing the pressure of a circulating fluid containing carbon dioxide obtained in the mixing step and conducting the gas-liquid separation treatment of excess carbon dioxide gasified;
   pressurizing a circulating fluid after gas-liquid separation to a predetermined pressure;
   continuously supplying an epoxide in a liquid or solution form to the circulation path; and
   mixing the epoxide supplied in the epoxide supply step with the circulating fluid in a path.

12. The method according to claim 11, wherein:
   the reactor is configured as a fixed bed multi-stage reactor by two or more adiabatic reactors connected in series; and
   the circulation path is to return at least a portion of a fluid mixture in a liquid form flowed out through an outlet of a last stage reactor to a first stage reactor.

13. The method according to claim 12, further comprising:
   continuously supplying an epoxide in a liquid or solution form to at least one flow path among flow paths for connecting respective reactors included in the fixed bed multi-stage reactor; and
   mixing the epoxide supplied in the epoxide supply step with a fluid mixture in a liquid form flowed into a flow path in the flow path.

14. The method according to claim 13, comprising:
   removing heat from a fluid mixture in a liquid form flowed into at least one flow path among flow paths for connecting the respective reactors included in the fixed bed multi-stage reactor by indirect heat exchange.

15. The method according to claim 14, wherein the mixing of the carbon dioxide and the mixing of the epoxide is conducted with in-line mixers.

16. The method according to claim 13, wherein the mixing of the carbon dioxide and the mixing of the epoxides is conducted with in-line mixers.

17. The method according to claim 12, comprising:
   removing heat from a fluid mixture in a liquid form flowed into at least one flow path among flow paths for connecting respective reactors included in the fixed bed multi-stage reactor by indirect heat exchange.

18. The method according to claim 17, wherein the mixing of the carbon dioxide and the mixing of the epoxide is conducted with in-line mixers.

19. The method according to claim 12, wherein the mixing of the carbon dioxide and the mixing of the epoxide is conducted with in-line mixers.

20. The method according to claim 11, wherein the mixing of the carbon dioxide and the mixing of the epoxide is conducted with in-line mixers.

* * * * *